United States Patent [19]

Peik et al.

[11] Patent Number: 4,529,797
[45] Date of Patent: Jul. 16, 1985

[54] HETEROPOLYSACCHARIDE S-198

[75] Inventors: Jerry A. Peik, San Diego; Suzanna M. Steenbergen, Lakeside; Harold R. Hayden, Escondido, all of Calif.

[73] Assignee: Merck & Co., Inc., Rahway, N.J.

[21] Appl. No.: 587,733

[22] Filed: Mar. 8, 1984

Related U.S. Application Data

[63] Continuation of Ser. No. 355,933, Mar. 8, 1982, abandoned, which is a continuation-in-part of Ser. No. 256,628, Apr. 23, 1981, abandoned.

[51] Int. Cl.$^3$ .................. C08B 37/00; C12P 19/06
[52] U.S. Cl. .................. 536/123; 435/104; 536/114; 536/1.1
[58] Field of Search .............. 536/1.1, 114, 123, 119

[56] References Cited

U.S. PATENT DOCUMENTS

| | | | |
|---|---|---|---|
| 3,960,832 | 6/1976 | Kang et al. | 536/123 |
| 4,211,774 | 7/1980 | Kang et al. | 536/123 |
| 4,304,906 | 12/1981 | Kang et al. | 536/123 |
| 4,326,053 | 4/1982 | Kang et al. | 536/123 |
| 4,342,866 | 8/1982 | Kang et al. | 536/123 |

*Primary Examiner*—Johnnie R. Brown
*Attorney, Agent, or Firm*—Gabriel Lopez; Hesna J. Pfeiffer

[57] ABSTRACT

A novel polysaccharide S-198 is disclosed composed of principally carbohydrate, 9–12% protein, and 2–4% O-acyl groups (calculated as O-acetyl). The carbohydrate portion comprises about 13–18% glucuronic acid and the neutral sugars mannose, glucose, and rhamnose in the approximate molar ratio 1:2:2. This polysaccharide is produced by a new Alcaligenes species ATCC 31853, in a suitable fermentation medium.

3 Claims, No Drawings

HETEROPOLYSACCHARIDE S-198

CROSS-REFERENCES

This is a continuation of application Ser. No. 355,933 filed Mar. 8, 1982, now abandoned, which is a continuation-in-part of U.S. Ser. No. 256,628 filed Apr. 23, 1981, now abandoned.

The following uses of S-198, described herein, are claimed in three other applications, filed on Mar. 8, 1982, and identified as follows.

| Ser. No. | Title | Inventors |
|---|---|---|
| 355,932 | Use of S-198 in High Water Base Fluids | J. Shim and J. Chang |
| 355,300 | Use of S-198 in Well Treating Fluids | P. Pickens and J. Shim |
| 355,299 | Use of S-198 in Flowable Pesticides | G. Golegrove and J. Shim |

BACKGROUND OF THE INVENTION

It is known that heteropolysaccharides can be produced by certain microorganisms. Some of these heteropolysaccharides function as hydrophilic colloids and because of their viscosity and rheology properties have been used as thickening agents for aqueous systems.

As with other fields of technology, research has continued with the objective of discovering new heteropolysaccharides having useful properties as thickening, suspending and/or stabilizing agents. It is an object of this invention to provide a new heteropolysaccharide. It is another object to provide a method for making this new compound. A still further object is provision of formulations containing the new heteropolysaccharide as a thickening or suspending or stabilizing agent. Other objects of the invention will become evident from the ensuing description of this invention.

SUMMARY OF THE INVENTION

The present invention pertains to a novel heteropolysaccharide which is produced by the action of a bacterium on a selected carbon source. Further, the invention pertains to a novel process for producing the heteropolysaccharide by bacterial fermentation of a selected carbon source and fermentation medium ingredients under controlled conditions. The heteropolysaccharide of this invention is a high molecular weight polysaccharide containing primarily carbohydrate. It is sometimes referred to as a "gum" but it is believed that the heteropolysaccharide terminology is more accurate and precise. In the following description of the invention, it will sometimes be referred to as Heteropolysaccharide S-198 or simply S-198.

This novel compound may be prepared by fermentation of a suitable nutrient medium with an organism, an Alcaligenes species. An unrestricted permanent deposit of an organism of this species employed in making the heteropolysaccharide was made with the American Type Culture Collection on March 31, 1981 under Accession No. ATCC 31853.

The organism was isolated from a pond water sample obtained in the Rocky Mountains near Denver, Colo. The organism was picked as a gummy colony after five days' incubation at 30° C. from a YM agar plate. The isolate was then pure cultured on nutrient agar.

Taxonomic studies of ATCC 31853 indicate that it does not correspond to any of the Alcaligenes species in Bergey's Manual.

A YM flask seed was started with a fresh NA plate and placed on a gyrotary shaker at 30° C. Approximately 24 hrs. later this seed was used to inoculate an E-1 flask with 3% hydrolyzed starch as the carbon source. This flask was also placed on a shaker at 30° C. Approximately 72 hrs. later the flask was noted to have viscous beer and upon addition of two volumes of 99% IPA a fibrous precipitate was observed.

Another YM seed flask was prepared in the above fashion and used at 24 hrs. to inoculate five flasks containing various media and 3% glucose. These flasks were incubated on a shaker at 30° C. for about 72 hrs. at which the pH, viscosity, gum yield, and product viscosity were measured. The results are shown in Table 1.

E-1 medium contains 5 gms of dipotassium phosphate, 0.1 gm of magnesium sulfate, 0.9 gm of ammonium nitrate, 0.5 gm of Promosoy 100 (an enzymatic digest of soybean meal sold by Central Soya Chemurgy Division), 30 gms of dextrose and 1 liter of tap water. The pH of the E-1 medium is about 7.6 to 7.8.

TABLE 1
EFFECT OF MEDIA ON GUM PRODUCTION

| Medium | pH | Beer Vis. (cP) | Gum Yield (%) | 1% Product Vis. (cP) |
|---|---|---|---|---|
| E-1 | 6.3 | 4800 | 1.144 | 1950 |
| E-1 − NH$_4$NO$_3$ + 0.19% NaNO$_3$ | 6.7 | 2050 | 0.976 | ND[1] |
| E-1 + 0.15% Promosoy | 5.4 | 5400 | 1.602 | 1900 |
| E-1 + HoLe[2] salts | 6.3 | 3000 | 0.934 | ND |

| | Conc. In Stock Soln. (Mg/L) | Conc. In Final Medium (ppm) |
|---|---|---|
| H$_3$BO$_3$ | 285.0 | 0.05 B$^{+3}$ |
| MnCl$_2$4H$_2$O | 1800 | 0.5 Mn$^{+2}$ |
| FeSO$_4$ | 1360 | 0.5 Fe$^{+2}$ |
| Na$_2$C$_4$H$_4$O$_6$.2H$_2$O (Na Tartrate) | 2098 | |
| CuCl$_2$ | 26.9 | 0.01 Cu$^{+2}$ |
| ZnCl$_2$ | 20.8 | 0.02 Zn$^{+2}$ |
| CoCl$_2$.6H$_2$O | 73.99 | 0.01 Co$^{+2}$ |
| Na$_2$MoO$_4$.2H$_2$O | 25.2 | 0.01 Mo$^{+6}$ |

[1]ND: Not determined
[2]Hole salts: An aqueous solution comprising

FERMENTATION CONDITIONS

Heteropolysaccharide S-198 is produced during the aerobic fermentation of suitable aqueous nutrient media under controlled conditions via inoculation with the organism ATCC 31853. The media contain a source of carbon, nitrogen, and inorganic salts.

In general, carbohydrates (for example, glucose, fructose, maltose, sucrose, xylose, mannitol and the like) can be used either alone or in combination as sources of assimilable carbon in the nutrient medium. The exact quantity of the carbohydrate source or sources utilized in the medium depends in part upon the other ingredients of the medium but, in general, the amount of carbohydrate usually varies between about 2% and 5% by weight of the medium. These carbon sources may be combined in the medium. In general, many proteinaceous materials may be used as nitrogen sources in the fermentation process. Suitable nitrogen sources include, for example, yeast hydrolysates, primary yeast, soybean meal, cottonseed flour, hydrolysates of casein, corn-steep liquor, distiller's solubles or tomato paste and the like. The sources of nitrogen, either alone or in combination, are used in amounts preferably ranging from about 0.05% to 0.2% by weight of the aqueous medium. Promosoy 100 can be used in the range 0.005 to 0.4%.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the media described in the examples are merely illustrative of the wide variety of media which may be employed, and are not intended to be limiting.

As an alternate medium, S-198 may be grown under low $Ca^{+\cdot}$ conditions, i.e., in deionized water or some other aqueous system substantially free of $Ca^{++}$ (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 31853 culture and producing the polysaccharide S-198 can vary from about 6 to 8.

Although the polysaccharide S-198 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol, conveniently in the form of CBM (an 85:15 alcohol:water constant boiling mixture).

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing the S-198 is particularly suited for the preparation of large quantities.

Although ATCC 31853 can be grown under a broad spectrum of media conditions, the following preferred conditions are recommended.

1. CULTURE MAINTENANCE

The culture grows quite well on nutrient agar (NA) or YM agar, but NA is preferred for culture maintenance.

2. SEED PREPARATION

Seed preparation for this organism is started in 500 ml flasks containing 100 ml YM medium incubated at 30° C. The YM seeds are then used at 24-30 hrs to inoculate a 5 L fermentor containing 3 L of the seed medium. The composition of the seed medium is as follows:

| | |
|---|---|
| 3.0% | Glucose |
| 0.5% | $K_2HPO_4$ |
| 0.06% | Promosoy 100 |
| 0.12% | $NH_4NO_3$ |
| 0.01% | $MgSO_4.7H_2O$ |
| 0.1 ml/L | HoLe Salts |
| 2 ml | antifoam additive |

A 5 to 10% inoculum size is used at 48 hrs to inoculate the final fermentor, containing 50 L of medium.

3. 70 L FERMENTOR MEDIUM

| | |
|---|---|
| 3.0% | Glucose |
| 0.05% | $K_2HPO_4$ |
| 0.06% | Promosoy 100 |
| 0.12% | $NH_4NO_3$ |
| 0.01% | $MgSO_4.7H_2O$ |
| 0.1 ml/L | HoLe Salts |
| 20 ml | antifoam additive |

The pH is controlled at 6.5-7.2, preferably 6.8; the temperature at 30° C. Aeration is 20 L/min. Agitation is employed starting at 300 rpm increased to 600 rpm at 20 hrs. and then increased to 800 rpm at 44.5 hr.

Fermentation times range from 60-70 hrs with beer viscosity ranging from 3500 cP to 4800 cP. Conversion efficiencies vary from 44-55% with 3% glucose. Antifoam SAG 471 (Union Carbide) is used. A particular fermentation under these conditions lasted 69 hours.

4. RECOVERY

On completion of the fermentation, the heteropolysaccharide S-198 may be recovered by treatment of the fermentation beer with a miscible solvent which is a poor solvent for the heteropolysaccharide and does not react with it. In this way the heteropolysaccharide is precipitated from solution. The quantity of solvent employed generally ranges from about 2 to about 3 volumes per volume of fermentation beer. Among the various solvents which may be employed are acetone and lower alkanols such as methanol, ethanol, isopropanol, n-butanol, sec-butanol, tertiary butanol, isobutanol, and n-amyl alcohol. Isopropanol is preferred. Typically, the fermentation beer is heated to a temperature of about 70° C. to 75° C. for a short time (e.g., about 10 to 15 minutes), and then cooled to about 30° C. or lower before addition of the solvent. A spent alcohol concentration of 57-59% is required for precipitating the heteropolysaccharide from the fermentation beer. The solid is recovered by separating it from the liquid, as by filtering or straining, and then drying at elevated temperature. This particular fermentation batch was pasteurized at 75° C. for 15 minutes and then precipitated with approximately 2 volumes of isopropanol.

5. DRYING

The product is dried at 55° C. for up to one hour in a forced-air tray drier.

6. PRODUCT QUALITY

Typical one percent deionized water viscosities range from 1200-1600 cP as measured on a Brookfield LVF, spindle 3, 60 rpm at 25° C.

The results from one fermentation are given below.

| Age (hr.) | pH | Visc. (cP) | Residual Carbon Source | Yield |
|---|---|---|---|---|
| 20 | 6.4 | 1300 | 1.98% | 0.53% |
| 44.5 | 6.5 | 2900 | 0.81% | 1.20% |
| 69 | 6.6 | 3650 | 0.30% | 1.46% |

Viscosities are measured on a Brookfield LVF viscometer at 60 rpm, room temperature, with spindle 2 (<500 cP), 3 (500-2000 cP), or 4 (>2000 cP).

HETEROPOLYSACCHARIDE S-198

The heteropolysaccharide produced by ATCC 31853 is composed of principally carbohydrate, 2-4% (calculated as O-acetyl) O-acyl groups, substantially no pyruvate, and about 9-12% protein.

The carbohydrate portion of the S-198 polysaccharide contains 13.0-17.6% glucuronic acid (based on wt. gum) and the neutral sugars mannose, glucose, and rhamnose in the approximate molar ratio of 1:2:2.

Colloidal titration (DIMDAC/sulphonic acid method) indicates the gum is acidic (0.58% equivalents of anionic groups/g. gum). Potentiometric titration indicates 0.65 mequiv./gm.

The acetyl content of 2-4% was determined by treating a 0.2% aqueous solution of S-198 gum with an alkaline, hydroxylamine reagent followed by treatment with an acidic ferric chloride reagent [S. Hestrin (1949) J. Biol. Chem. 180 249-261].

Liquid chromatography (Bio-Rad Organic Acid Analysis Column) was used to further identify the O-acyl groups. Using this technique the O-acyl groups of S-198 have been found to be primarily O-acetyl and O-succinyl, and substantially free of O-formyl.

The neutral sugars of polysaccharide S-198 were determined by dissolving ten mg. of the product in 2 ml 2N $H_2SO_4$, and the mixture is heated at 100° C. for 4 hours. The resulting solution is cooled, neutralized with barium hydroxide and the pH is brought to 5-6 with solid carbon dioxide. The resulting precipitate of barium sulfate is removed by centrifugation and the supernatant is concentrated to a syrup under reduced pressure. The sugars in the hydrolysate are tentatively identified by gas-liquid chromatography of their aldononitrile acetate derivatives on a Hewlett-Packard Model 5830A chromatograph using 3% by weight OV-225 on 80/100 mesh Gas Chrom Q at 210° C. The sugars are identified and quantitated by comparison with authentic standards [J. K. Baird, M. J. Holroyde, and D. C. Ellwood (1973) Carbohydr. Res. 27 464-467]. See Table 2 for determination of neutral sugars.

TABLE 2

| Total Neutral Sugars in S-198 ||
|---|---|
| Sugar | Wt. % |
| Rhamnose | 38-42 |
| Glucose | 39-43 |
| Mannose | 16-19 |

The various neutral sugars of the polysaccharides were also characterized by use of descending paper chromatography of Whatman No. 1 chromatography paper using as the solvent the upper layer of pyridine-:ethyl acetate:water (2:5:5). Chromatograms were stained using silver nitrate dip and acid aniline phthalate spray reagent. Component sugars were identified by co-chromatography with sugar standards and by the specific-color reaction with the aniline phthalate reagent.

The glucuronic acid content of the polysaccharide was determined by decarboxylation with 19% hydrochloric acid, followed by trapping the liberated carbon dioxide in standard sodium hydroxide and back titration [B. L. Browning (1967) Methods of Wood Chemistry II, 632-633]. The decarboxylation method gave the value 17.6, 13.1, and 14.9% for three different samples of S-198.

Paper electrophoresis was used for the separation and tentative identification of the uronic acids present in the neutralized acid hydrolysate described above. Aliquots of this and known uronic acid standards were applied to Camag electrophoresis paper No. 68-011 and electrophoresis was carried out for 2.0 hours in a pH 2.7 buffer using a Camag Model HVE electrophoresis apparatus. Chromatograms were air dried and stained with silver nitrate dip reagent to locate the uronic acids being separated. Two uronic acid spots were found by this method which had the relative mobilities of glucuronic acid and mannuronic acid standards, the latter spot representing an acid resistant uronic acid-containing disaccharide.

An infrared spectrum of native S-198 was made on dried material in a KBr pellet. The heteropolysaccharide evidenced peaks at: 1725 $cm^{-1}$ and 1625 $cm^{-1}$ indicating ester and carboxyl groups, respectively.

A sample of S-198, BD-791, was dialyzed and freeze dried after fermentation. The sample was methylated according to the procedure used in Sanford and Conrad, Biochemistry 5 (1966) 1508-1517).

Approximately 40 mg of sample was weighed into dry 100 ml serum bottles before inserting a rubber serum cap. Then ca. 40 ml of dimethyl sulfoxide (DMSO) (redistilled and dried over 4A molecular sieves) was added via a syringe. The sample was continuously flushed with dry nitrogen. In order to dissolve the sample, it was necessary to heat the solution. To the vial was added 20 ml anion solution made from DMSO and NaH (2.5 g/50 ml DMSO). The sample was placed in sonic water bath for ca. 30 min before leaving at room temperature overnight. The solution was cooled and then 20 ml $CH_3I$ was added via a syringe. After stirring for at least one hour, the excess $CH_3I$ was rotovaped off before dialysis (DI water) and concentrating to dryness (rotovap).

The sample was hydrolyzed using 90% formic acid/0.13M $H_2SO_4$. The resulting sugars were reduced with $NaBH_4$ and the resulting alditols were acetylated with acetic anhydride/pyridine (1:1) at 100° C.

The methyl sugars as their aditol acetates were separated by gas chromatography. Apparent identities were deduced by looking at both retention times (RT) and mass fragmentation patterns. The relative amounts of the methyl derivatives of glucose, mannose, and rhamnose are given in Table 3. Based on the amounts of the neutral sugars found (Table 2), it is believed that the 2,6-diemthyl sugar (Table 3) is 2,6-dimethyl glucose.

Fragments released by mild acid were also analyzed. A sample of S-198 was hydrolyzed under mild conditions (1.0N $H_2SO_4$, 100° C.) and the resulting fragments were separated by paper chromatography (pyridine-:ethyl acetate:water (2:5:5), upper phase). Based on chromatograms developed with silver nitrate, S-198 was found to give spots corresponding in mobility to the reducing sugars rhamnose, mannose, glucose, glucuronic acid and a low proportion of an additional but unidentified fast moving component ($R_{Glc}=3.30$).

TABLE 3
Relative Amounts of Methyl Sugars in S-198

| Methyl Sugars | | Wt. % | Linkage | Approx. Moles |
|---|---|---|---|---|
| 2,3,4 Me$_3$ | Rhamnose | 27.5 | Terminal | 2 |
| 2,6 Me$_2$ | Rhamnose | 14.2 | 1,4 | 1 |
| 2,4,6 Me$_3$ | Glucose | 13.3 | 1,3 | 1 |
| 2,3,6 Me$_3$ | Glucose | 4.1 | 1,4 | — |
| 2,3,6 Me$_3$ | Mannose | 21.7 | 1,4 | 1 |
| 2,6 Me$_2$ | Glu/Man | 19.3 | 1,3,4 | 1 |

Heteropolysaccharide S-198 has the following profile of properties (all measurements are at room temperature):

1. VISCOSITY (Brookfield LVT Viscometer)

| Conc. | Spindle | RPM | Tap $H_2O$ | Viscosity (cP) Tap $H_2O$ + 0.1% KCl |
|---|---|---|---|---|
| 1.0% | 4 | 60 | 2,450 | 2800 |
| — | 4 | 6 | 16,000 | — |
| 0.1% | 1 + UL adap. | 6 | 76 | 75 |
| 0.5% | (Wells-Brookfield) | — | 590 | 560 |

2. SHEAR (Wells-Brookfield Microviscometer RVT-c/P)

1. n @ 1.92 sec$^{-1}$ 10,560 cP
2. n @ 9.6 sec$^{-1}$ 2,560 cP
3. n @ 76.8 sec$^{-1}$ 320 cP
4. n @ 384 sec$^{-1}$ >64 cP
5. n @ 384 sec$^{-1}$ >64 cP
6. n @ 9.6 sec$^{-1}$ 1880 cP

3. 40° F. STORAGE STABILITY (4 Weeks)

Week 4: 2600 cP, Brookfield LVT, spindle No. 4, 60 rpm; no gelation.

4. ACID, BASE, HEAT, STABILITY

A. Stability

| | Initial n | Final n | % Change | |
|---|---|---|---|---|
| 1. Acetic acid plus heat | 2700 cP | 2950 cP | +9 | Brookfield |
| 2. 1% HCl plus heat | 1040 cP | 1200 cP | +15 | " |
| 3. 1% NaOH plus heat | 680 cP | 2200 cP$^{(a)}$ | +224 | Wells-Brookfield |
| 4. Heat only | 1410 cP$^{(b)}$ | 1550 cP$^{(c)}$ | +10 | " |

(a) gel  (b) 0.75% soln.  (c) softgel

B. pH Effect (Wells-Brookfield RVT-cP @ 9.6 sec$^{-1}$

| 1. 5% Acetic acid | 2.61 | pH | 2230 cP |
|---|---|---|---|
| 2. 5% $NH_4OH$ | 11.15 | pH | 2560 cP |

5. SALT & DYE COMPATIBILITY

A. Salt

| 1. $CaCl_2$ (Saturated) | Compatible | 5. 1% $CaCl_2.2H_2O$ | Compatible |
|---|---|---|---|
| 2. Amm. polyphosphate | Precipitate | 6. 1% KCl | Compatible |
| 3. 60% $NH_4NO_3$ | Compatible | 7. 0.1% KCl | 990 cP$^{(d)}$ |
| 4. 1% $Al_2(SO_4)_3.18H_2O$ | Compatible | 8. 2.5% KCl | 1380 cP$^{(d)}$ |

(d) Wells-Brookfield RVT-c/P @ 9.6 sec$^{-1}$

B. Dyes

| 1. Milling Green | Compatible | 2. Methylene Blue | Precipitate |
|---|---|---|---|

6. TEXTURE/FLOW PROPERTIES

Chunky, discontinuous flow, no gelation, not gummy to the touch.

7. SYNERGISM & ENZYMES (Wells-Brookfield RVT-cP at 9.6 sec$^{-1}$)

| | 1% n | 0 hour n of mixture | 2 hour n of mixture | Expected viscosity | Synergism |
|---|---|---|---|---|---|
| A. Guar | 2050 cP | 1740 cP | 1920 cP | 1700 cP | +13% |
| B. H.P. Guar | 2230 cP | 1840 cP | 2020 cP | 1790 cP | +13% |
| C. CMC | 560 cP | 850 cP | 720 cP | 890 cP | None |
| D. HEC | 440 cP | 1100 cP | 770 cP | 790 cP | None |

8. MILK REACTIVITY

A. Dispersion: Excellent
B. Whey off: 1st day

9. FILM FORMATION

Medium tensile strength; rough texture; eneven consistency; uneven pull down; plastic film formed.

Cross-linking of S-198 with various polyvalent ions was tested by preparing 0.4% S-198 solutions in 2% KCl tap water. To 200 ml of these solutions were added, respectively: (1) 1.0 gm chrome alum crystal dissolved in 5 ml $H_2O$; (2) 1.0 gm aluminum sulfate dissolved in 5 ml $H_2O$; (3) 1.5 ml Zircomplex ® (Manchem, Manchester), liquid zirconium; (4) 1.5 ml Tysor LA (Dupont), organic titanate; and (5) 0.5 gm $FeCl_3$ dissolved in 5 ml $H_2O$. These solutions were allowed to stand for 15 min., then checked for cross-linking. If no cross-linking was observed, the pH was raised to 9.0 using 15%

NaOH and the solutions re-checked. Fresh solutions were prepared and the pH's adjusted with either 15% NaOH or 15% HCl to 4, 7, and 9 and checked for cross-linking after 15 min. S-198 did not cross-link under any of these conditions with $Cr^{+3}$ or $Al^{+3}$. It did cross-link with $Zr^{+4}$, $Ti^{+4}$, and $Fe^{+3}$ but only at pH 9.0. Cross-linking was evidenced by weak or moderate gelation.

The polysaccharide S-198 imparts viscosity to aqueous media when dissolved in water in low concentrations. It is useful as a thickening, suspending, emulsifying, stabilizing, lubricating, film-forming, or binding agent, especially in aqueous systems. In particular, it has uses in the following applications or products: adhesives, wall-joining cements, water-retentive grouts and mortars, spackling compounds, can sealing, boiler compounds, latex creaming, welding-rod fluxes, brazing pastes, ceramic glazes and extrusions, cleaners and polishes, toys, emulsions (latex, asphalt, silicone), silver recovery, seed coatings, spray control for pesticides or herbicides, emulsifiable concentrated and flowable pesticides and herbicides, tobacco binders, water-based inks, lithographic fountain solutions, leather finishes, hydro-mulching and hydro-seeding, textile printing and finishing, wet-end paper additives, wet-end paper retention and formation aid, anti-stick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

Also this gum has utility in food systems such as jellies and other high sugar systems, beverages including citric acid based drinks, dairy products including ice cream and yogurt, salad dressings, dry mixes, icings, ang glazes, syrups, puddings, farinaceous foods, canned and retorted foods, and bakery fillings.

In paper applications S-198 could be used, for example, in a pigmented clay coating of the following formulation:

| | |
|---|---|
| Pigment (Satin White) | 10% |
| Clay | 90% |
| S-198 | 0.5% |
| Latex | 10 pts/100 pts/pigment |
| Soy proteins | 5 pts/100 pts/pigment |

These ingredients are mixed with sufficient water to produce an easily applicable paper coating.

S-198 can be used in no-oil, low-oil, or high-oil salad dressings. Typical formulations are:

| | PERCENT |
|---|---|
| No-oil Dressing | |
| Water | 50.90 |
| Cider vinegar (50-grain) | 29.80 |
| High Fructose corn syrum | 10.00 |
| Lemon juice, single strength | 5.00 |
| Salt | 2.20 |
| Spices & Other ingredients | 1.40 |
| Sodium Citrate | 0.10 |
| S-198 | 0.325 |
| 6% Oil Dressing INGREDIENTS | |
| H2O | 56.10 |
| Vinegar (50 grain) | 18.00 |
| Tomato paste (26%) | 7.50 |
| Vegetable oil | 6.00 |
| Lemon juice | 5.00 |
| Salt | 3.50 |
| Egg yolk (fresh) | 2.00 |
| S-198 | 0.45 |
| Spices and other ingredients | 1.3 |
| 38% Oil Dressing INGREDIENTS | |
| Vegetable oil | 38.00 |
| H2O top | 36.50 |
| Sugar (white, 100 grain) | 9.00 |
| Salt | 2.00 |
| Paprika | 1.35 |
| Mustard | 1.25 |
| S-198 | 0.40 |

Because of a tendency to gel, less than 0.4% S-198 is recommended in high oil salad dressings.

In addition to the basic properties described above, S-198 has been found to possess the unusual property of high viscosity retention even after high shear and/or heat treatment. This property is valuable for a number of industrial applications, such as high water based lubricating fluids (HWBF), and various oil field applications such as circulating drilling fluids, fracturing or acidizing fluids, or workover and completion fluids, and as a thickener and suspending agent in flowable pesticides or other agricultural suspensions.

For instance, a solution of 0.28 % of biogum S-198 (a blend of three different fermentation batches in equal amounts) had an initial viscosity of 193 (LVT Brookfield, rm. temp., sp. no. 2, 60 rpm). Each of several samples was passed through a piston-type, air operated, boost pump: 6 passes at 2000 psi, and 1 pass at each 3000 psi, at 4000 psi, and 5000 psi. Representative viscosity results are as indicated, which show good shear stability.

| | 2000 psi | | | | | | 3000 psi | 4000 psi | 5000 psi |
|---|---|---|---|---|---|---|---|---|---|
| | 1 | 2 | 3 | 4 | 5 | 6 | | | |
| Visc. | 208 | 232 | 222 | 215 | 198 | 193 | 235 | 229 | 222 |

A typical HWBF composition has 90–95% water, a shear stable viscosity imparting amount of S-198 gum (0.1–2%), and about 3–9% of one or more additives which are wetting agents, defoamers, corrosion inhibitors, anti-wear agents, and biological control agents. Optionally, up to 33% anti-freeze may be added.

S-198 can be used at 0.07–1% in well treating fluids, by which is meant a variety of compositions such as circulating drilling fluids, workover and completion fluids and stimulation fluids (such as hydraulic fracturing and acidizing fluids).

Typical fluid fermentations are:

| | | |
|---|---|---|
| 1. | Seawater | 1 bbl |
| | S-198 | 0.25–3.5 lb |
| | NaOH | to ca. pH 9 |
| | Starch (optional) | 1 lb |
| 2. | Fresh Water | 1 bbl |
| | S-198 | 0.25–3.5 lb |
| | KCl | 3.5–17.5 lb |
| | Bentonite | 2–20 lb. |
| | NaOH | to ca. pH 9 |
| | CMC (optional) | ½ lb |
| 3. | Aq. HCl (1–15 wt. %) 99% | |
| | Corrosion inhibitor | 0.05% |
| | S-198 | 0.1–1.0% |

Flowable pesticides refers to aqueous suspensions of insoluble, often hydrophobic, materials which are used as insecticides, herbicides, fungicides, miticides, and aquaherbicides. These products typically require extensive milling to intimately mix the components into concentrated suspensions which are then diluted with water prior to use. A typical concentrate formulation is:

|  | Wt. % |
|---|---|
| Water | 30–60 |
| Antifreeze | 3–10 |
| Surfactant | 1–3 |
| Dispersant | 1–4 |
| Antifoam | 0.25–1 |
| Active material | 10–60 |
| S-198 | 0.08–0.25 |

EXAMPLE 1

PREPARATION OF S-198

2. SEED PREPARATION

ATCC 31853 was started in a 500 ml flask containing 100 ml YM medium incubated at 30° C. The YM seeds were then used at 24–30 hrs. to inoculate a 5 L fermentor containing 3 L of the seed medium. The composition of the seed medium is:

| 3.0% | Glucose |
|---|---|
| 0.5% | $K_2HPO_4$ |
| 0.05% | Promosoy 100 |
| 0.09% | $NH_4NO_3$ |
| 0.01% | $MgSO_4.7H_2O$ |
| 2 ml | antifoam additive (SAG) |

A 12% inoculum was used at 24 hrs. to inoculate the final fermentor, containing 20 L of medium.

2. 30 L FERMENTOR MEDIUM

| 3.0% | Glucose |
|---|---|
| 0.05% | $K_2HPO_4$ |
| 0.05% | Promosoy 100 |
| 0.09% | $NH_4NO_3$ |
| 0.01% | $MgSO_4.7H_2O$ |
| 2 ml | antifoam additive (SAG) |

The pH is controlled at 6.6–6.8; the temperature is 30° C. Aeration is 10 L/min. Agitation is 300 rpm to start, increased to 700 rpm at 24 hr. Fermentation was stopped at 145 hr., giving a beer with a viscosity of 3000 cP. The gum yield was 1.19%. Recovery of the polysaccharide was with 2–3 volumes of IPA. The solid was recovered and then dried at elevated temperature. The product was identified as BD-791. It exhibited a 1% viscosity of 1580 cP.

EXAMPLE 2

S-198 TAXONOMY

A. Morphological Observations

1. Colonial Morphology

In nutrient agar, small colonies appeared in two days, and the diameter of the colonies reached approximately 1.2 mm after three days' incubation. The colony was yellow pigmented (non-diffusible), round, smooth, entire, convex and opaque. A hard membranous film was formed, some colonies became umbonate after prolonged incubation.

On YM agar, small mucoid colonies appeared in two days, and the diameter of the colonies reached approximately 2.5 mm after three days' incubation. The colony was yellow pigmented (non-diffusible), round, smooth, entire, more drop-like and opaque. The texture of the colony became very membranous, and, entire colonies were often removed when they were pushed by inoculation needles.

2. CELLULAR MORPHOLOGY

The strain was a Gram-negative rod shaped bacterium, motile by peritrichous flagella. On nutrient agar, the size of the cell was 0.5–0.6 by 1.2–8μm, the cell was straight and often had tapered ends. Elongation as well as pleomorphism were often seen after prolonged incubation.

On YM agar, the cell was straight, but more round-ended. The size of the cell was 0.4–0.6 by 0.9–2.4μm. Pallisade arrangement of the cells was often seen in the Zooglea-like mass.

Capsule, spore, accumulation of poly-β-hydroxybutyrate and volutin granules were not observed. Acid fast stain was negative.

3. GROWTH IN BROTH CULTURE

Growth of the strain was limited only on the surface. Pellicle was formed in both nutrient and YM broths in test tube culture.

B. PHYSIOLOGICAL AND BIOCHEMICAL TESTS

The following is a summary of results of physiological and biochemical tests employed which are listed in Table 4. Both cytochrome oxidase and catalase were positive. The organisms utilize glucose oxidatively, but not fermentatively. No anaerobic growth was observed. The organisms could grow at temperatures between 30° and 37° C., but not at 4° or 40° C. No survival was observed after incubation at 60° C. for 30 minutes. Maximum concentration of NaCl for tolerance test was 1.5%. The organisms grew at both pH's 6 and 8, but not at pH's 4 and 10.

On TSI agar, growth was observed on the slant only, but neither acid nor alkali reaction was observed. Litmus milk was peptonized and acid was produced. No $H_2S$ was produced from either cystic broth and TSI agar. Ammonia was produced from peptone. The organism hydrolyzed starch, gelatin, esculin, Tween 80, but not casein and pectin. 3-Ketolactose and Congo Red absorption tests were negative. The organisms were tolerant to 0.02 and 0.1% of triphenyltetrazolium chloride.

C. NUTRITIONAL TESTS

Growth factors were not required for their growth. Ammonium salt served as sole nitrogen source.

A total of 129 substrates were employed for nutritional tests, of which thirty (30) substrates were utilized by the organisms as carbon source and energy.

| D-Xylose | Cellobiose | Sebacate |
|---|---|---|
| L-Arabinose | Lactose | L-Malate |
| L-Rhamnose | Inulin | DL-p-Hydroxybutyrate |
| D-Glucose | Gluconate | DL-Lactate |
| D-Mannose | Salicin | Meso-Inositol |
| D-Galactose | Acetate | p-Hydroxybenzoate |

-continued

| Fructose | Succinate | L-α-Alanine |
| Sucrose | Fumarate | DL-Isoleucine |
| Trehalose | Pimelate | L-Glutamate |
| Maltose | Agelate | L-Tyrosine |

The organism could not utilize alcohols and amines.

Edited by R. E. Buchanan and N. E. Gibbons, published by the Williams & Wilkins Company, Baltimore, 1974), this organism belongs to a member of the genus Alcaligenes. There were four species of the genus Alcaligenes listed in the manual, however, the strain S-198 does not belong to any of them. From this standpoint, it is concluded that the organism is a new species of the genus Alcaligenes.

TABLE 4

Results of Physiological an Biochemical Tests of Organism S-198

| Test | Results | Test | Results |
|---|---|---|---|
| Cytochrome oxidase | + | Growth at various NaCl concentrations: | |
| Catalase | + | | |
| Oxidative and Fermentative (OF) Tests | Oxidative | 0.5% (W/V) | + |
| | | 1.5% | + |
| | | 3.0% | − |
| Anaerobic growth | − | 6.0% | − |
| Acid production from various carbohydrates: | | 7.5% | − |
| | | 10.0% | − |
| Adonitol | − | Growth at various pH values: | |
| L-Arabinose | + | pH 4 | − |
| Dulcitol | + | pH 6 | + |
| Ethanol | − | pH 8 | + |
| Fructose | + | pH 10 | − |
| Galactose | + | pH 12 | − |
| D-Glucose | + | Indole Test | − |
| Inositol | − | Methyl Red (MR) Test | − |
| Inulin | − | Voges Proskauer (VP) Test | − |
| Lactose | − | Simmons' citrate Test | − |
| Maltose | + | Nitrate reduction | − |
| Mannitol | − | Litmus Milk Acid and | − |
| Mannose | + | Peptonized | |
| Melibiose | + | Arginine dihydrolase (ADH) Test | − |
| α-Methylglucoside | − | Lysine decarboxylase (LDC) Test | − |
| Raffinose | + | Ornithine decarboxylase ()DC) Test | − |
| Rhamnose | + | Ammonia From Pentone | + |
| Salicin | − | Phenylaline deaminase (PAD) Test | − |
| Sorbitol | − | $H_2S$ Production | − |
| Sucrose | + | Urease Test | − |
| Trehalose | − | Phosphatase Test | − |
| D-Xylose | + | Egg Yolk Test | − |
| Growth in TSI agar: | | Starch hydrolysis | + |
| Slant | No change | Gelatin hydrolysis | + |
| Butt | No growth | Casein hydrolysis | − |
| Gas Production | − | Esculin hydrolysis | + |
| $H_2S$ Production | − | Tween 80 hydrolysis | + |
| Growth at various temperatures: | | Pectin hydrolysis | − |
| | | 3-Ketolactose production | − |
| 4° C. | − | Congo Red Absorption | − |
| 30° C. | + | Growth with Triphenyltetrazolium Chloride: | |
| 37° C. | + | | |
| 40° C. | − | 0.02% | − |
| 43° C. | − | 0.10% | − |
| 45° C. | − | | |
| 50° C. | − | | |

Survival at 60° C. for 30 min

D. ANTIBIOTIC SUSCEPTIBILITY TESTS

The organism was susceptible to chlortetracycline, 5 μg; gentamicin, 10 μg; kanamycin, 30 μg; neomycin, 30 μg; novobiocin, 30 μg; penicillin, 10 units; tetracycline, 30 μg. The organism was susceptible to the following antibiotics, but resistant colonies appeared. They were carbenicillin, 100 μg; erythromycin, 15 μg; and polymyxin B, 300 units. The organism was resistant to colistin, 10 μg, and streptomycin, 10 μg.

E. IDENTIFICATION

The strain S-198 was a Gram-negative, rod shaped bacterium, motile by peritrichous flagella. The organism was strictly aerobic, glucose was utilized oxidatively, but not fermentatively. According to Bergey's Manual of Determinative Bacteriology (the 8th edition,

What is claimed is:

1. The heteropolysaccharide S-198, which is principally carbohydrate, comprising 2–4% (calculated as O-acetyl) O-acyl groups, said O-acyl groups being primarily O-acetyl and O-succinyl and substantially free of O-formyl, 13–17.6% glucuronic acid, and the neutral sugars mannose, glucose, and rhamnose in the approximate molar ratio 1:2:2, wherein the ratio of terminally linked rhamnose to 1,4 linked rhamnose is 2:1 and the mannose is principally 1,4 linked.

2. The heteropolysaccharide of claim 1 prepared by fermentation under controlled conditions of culture ATCC 31853, an Alcaligenes species.

3. The heteropolysaccharide of claim 1 prepared in a fermentation medium substantially free of $Ca^{++}$ ions.

* * * * *